(12) United States Patent
Papania et al.

(10) Patent No.: US 10,099,024 B2
(45) Date of Patent: Oct. 16, 2018

(54) NASAL DRY POWDER DELIVERY SYSTEM FOR VACCINES AND OTHER TREATMENT AGENTS

(71) Applicants: The United States of America, as represented by the Secretary, Department of Health and Human Services, Washington, DC (US); Creare, Incorporated, Hanover, NH (US)

(72) Inventors: Mark J. Papania, Lilburn, GA (US); James J. Barry, Hanover, NH (US); Mark C. Bagley, Grafton, NH (US); Darin A. Knaus, Lyme, NH (US); Eric M. Friets, Norwich, VT (US); Edward Moynihan, Plainfield, NH (US)

(73) Assignees: The United States of America, as represented by the Secretary, Department of Health and Human Services, Washington, DC (US); Creare, Incorporated, Hanover, NH (US)

( * ) Notice: Subject to any disclaimer, the term of this patent is extended or adjusted under 35 U.S.C. 154(b) by 841 days.

(21) Appl. No.: 14/409,379

(22) PCT Filed: Jun. 24, 2013

(86) PCT No.: PCT/US2013/047399
§ 371 (c)(1),
(2) Date: Dec. 18, 2014

(87) PCT Pub. No.: WO2014/004400
PCT Pub. Date: Jan. 3, 2014

(65) Prior Publication Data
US 2015/0136132 A1    May 21, 2015

Related U.S. Application Data

(60) Provisional application No. 61/665,778, filed on Jun. 28, 2012.

(51) Int. Cl.
*A61M 15/08* (2006.01)
*A61M 15/00* (2006.01)
(Continued)

(52) U.S. Cl.
CPC ............ *A61M 15/08* (2013.01); *A61M 15/00* (2013.01); *A61M 15/003* (2014.02);
(Continued)

(58) Field of Classification Search
CPC .......... A61M 15/0028–15/0041; A61M 15/08; A61M 15/085
See application file for complete search history.

(56) References Cited

U.S. PATENT DOCUMENTS 2,470,297 A    5/1949   Fields
3,991,761 A *  11/1976  Cocozza ........... A61M 15/0028
                                                128/203.15
(Continued)

FOREIGN PATENT DOCUMENTS

GB    2 395 909    6/2004
GB    2 467 388    8/2010
(Continued)

OTHER PUBLICATIONS

ONdrugDelivery on behalf of OptiNose, "Breath-actuated Bi-Directional Delivery Sets the Nasal Market on a New Course," (2005) ONdrugDelivery Ltd, as retrieved Aug. 10, 2005.
(Continued)

*Primary Examiner* — Valerie L Woodward
(74) *Attorney, Agent, or Firm* — Klarquist Sparkman, LLP

(57) ABSTRACT

A nasal delivery device can include air-receiving section that has a first passageway therethrough to allow air to pass
(Continued)

through the air-receiving section, a powder-reservoir receiving section sized to receive a powder reservoir, and a powder-delivery section that has a second passageway therethrough to allow aerosolized powder from the powder reservoir to pass through the powder-delivery section. The first passageway can have a first end and a second end, with the first end being further from the powder-reservoir receiving section and the second end being at or near the powder-reservoir receiving area. The second end of the air-receiving section can include a flattened region so that air exiting the air-receiving section has a generally flattened profile.

24 Claims, 13 Drawing Sheets

(51) Int. Cl.
A61M 16/12 (2006.01)
A61M 16/00 (2006.01)
A61M 16/20 (2006.01)
A61M 15/06 (2006.01)

(52) U.S. Cl.
CPC ........ *A61M 15/004* (2014.02); *A61M 15/009* (2013.01); *A61M 15/0013* (2014.02); *A61M 15/0028* (2013.01); *A61M 15/0035* (2014.02); *A61M 15/0091* (2013.01); *A61M 15/0098* (2014.02); *A61M 16/0045* (2013.01); *A61M 16/122* (2014.02); *A61M 16/20* (2013.01); *A61M 15/002* (2014.02); *A61M 15/0036* (2014.02); *A61M 15/06* (2013.01); *A61M 2202/064* (2013.01); *A61M 2205/195* (2013.01); *A61M 2205/583* (2013.01); *A61M 2205/6036* (2013.01); *A61M 2206/10* (2013.01); *A61M 2206/14* (2013.01); *A61M 2206/16* (2013.01); *A61M 2210/0618* (2013.01); *A61M 2210/0625* (2013.01)

(56) References Cited

U.S. PATENT DOCUMENTS

| | | | | |
|---|---|---|---|---|
| 5,666,948 | A * | 9/1997 | Matson | A61D 7/04 128/200.23 |
| 5,669,378 | A * | 9/1997 | Pera | A61M 15/0028 128/203.15 |
| 6,606,992 | B1 | 8/2003 | Schuler et al. | |
| 2002/0165482 | A1 | 11/2002 | Keldmann et al. | |
| 2006/0231094 | A1 | 10/2006 | Djupesland | |
| 2006/0289007 | A1 | 12/2006 | Williams et al. | |
| 2007/0256687 | A1* | 11/2007 | Niemi | A61M 15/0028 128/200.23 |
| 2008/0289629 | A1* | 11/2008 | Djupesland | A61M 15/0028 128/203.15 |
| 2009/0293873 | A1* | 12/2009 | Djupesland | A61M 15/0028 128/203.15 |
| 2010/0108058 | A1* | 5/2010 | Glusker | A61M 15/0028 128/200.14 |
| 2010/0258118 | A1* | 10/2010 | Morton | A61K 9/0075 128/203.15 |
| 2010/0288275 | A1 | 11/2010 | Djupesland et al. | |
| 2010/0300439 | A1 | 11/2010 | Djupesland et al. | |
| 2011/0088690 | A1 | 4/2011 | Djupesland et al. | |
| 2011/0126830 | A1 | 6/2011 | Djupesland | |
| 2013/0047985 | A1* | 2/2013 | Harris | A61M 15/0028 128/203.15 |
| 2014/0230817 | A1* | 8/2014 | Richardson | A61M 15/0028 128/203.15 |

FOREIGN PATENT DOCUMENTS

| | | |
|---|---|---|
| GB | 2 470 486 | 11/2010 |
| GB | 2470486 | 11/2010 |

OTHER PUBLICATIONS

European Examination Report, dated Jun. 22, 2016, for corresponding European Patent Application No. 13734610.2, 5 pages.
Response to European Examination Report, filed Oct. 26, 2016, for corresponding European Patent Application No. 13734610.2, 12 pages.

* cited by examiner

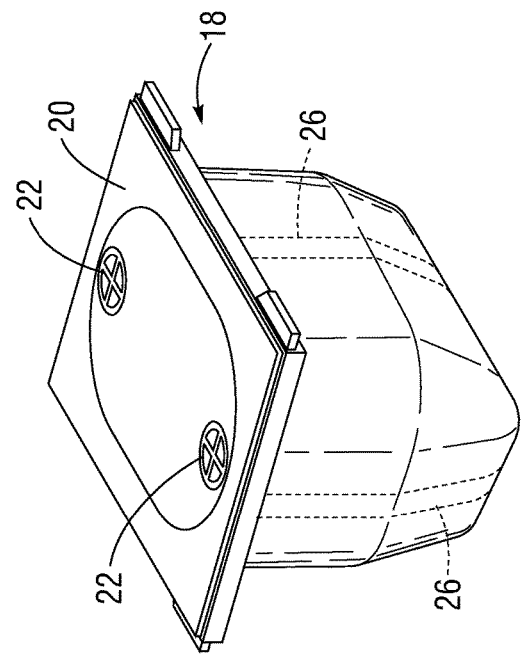
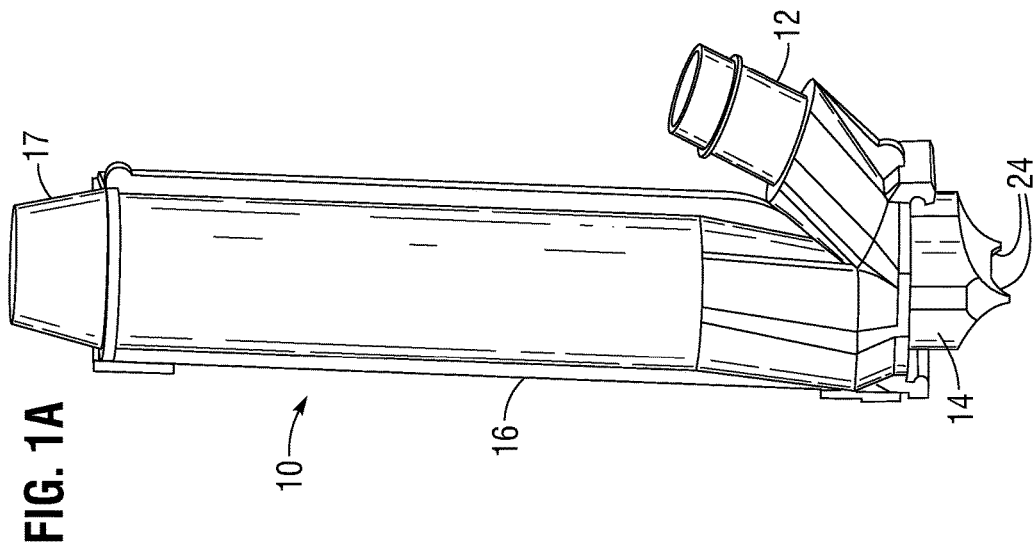

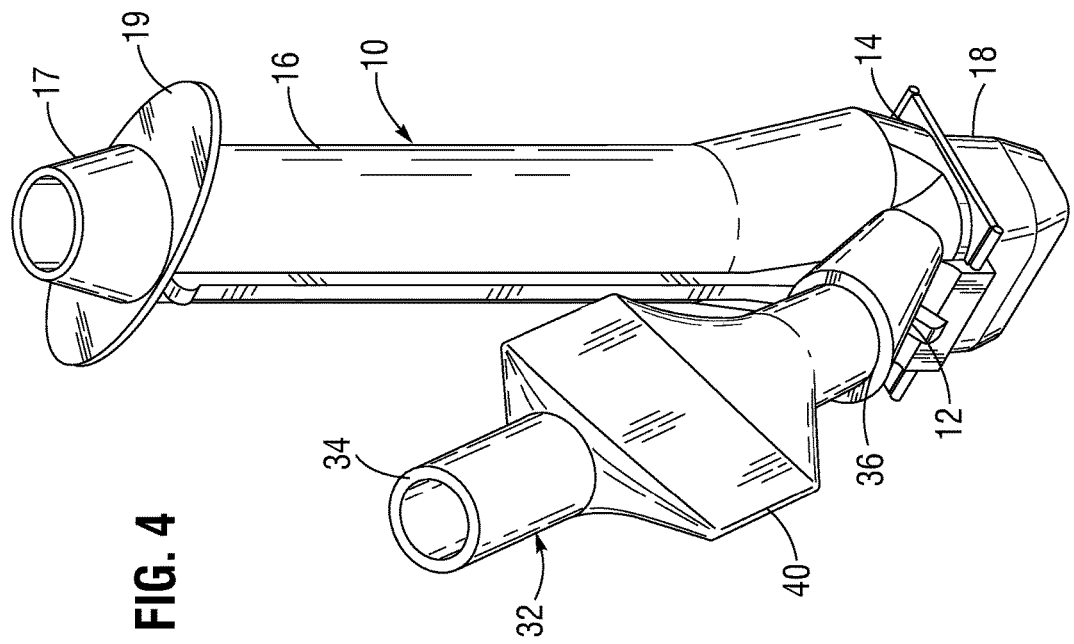

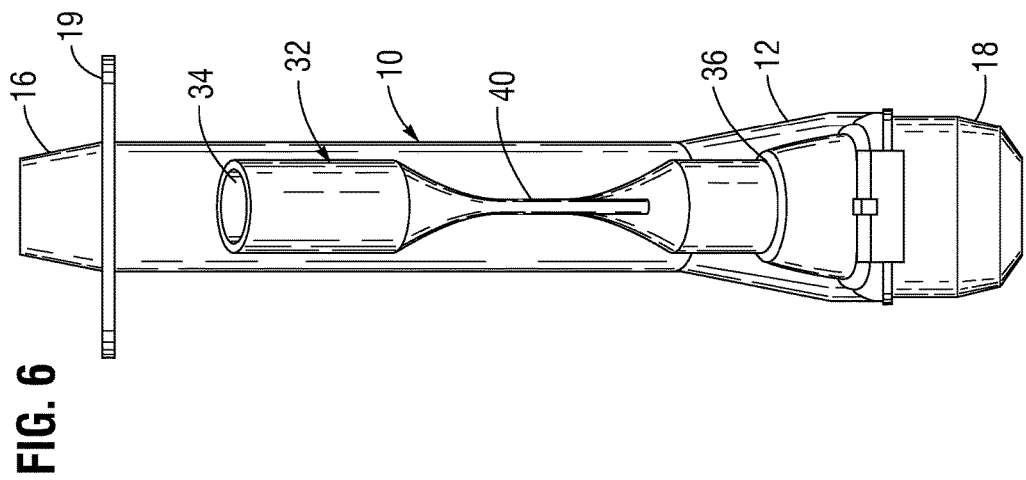

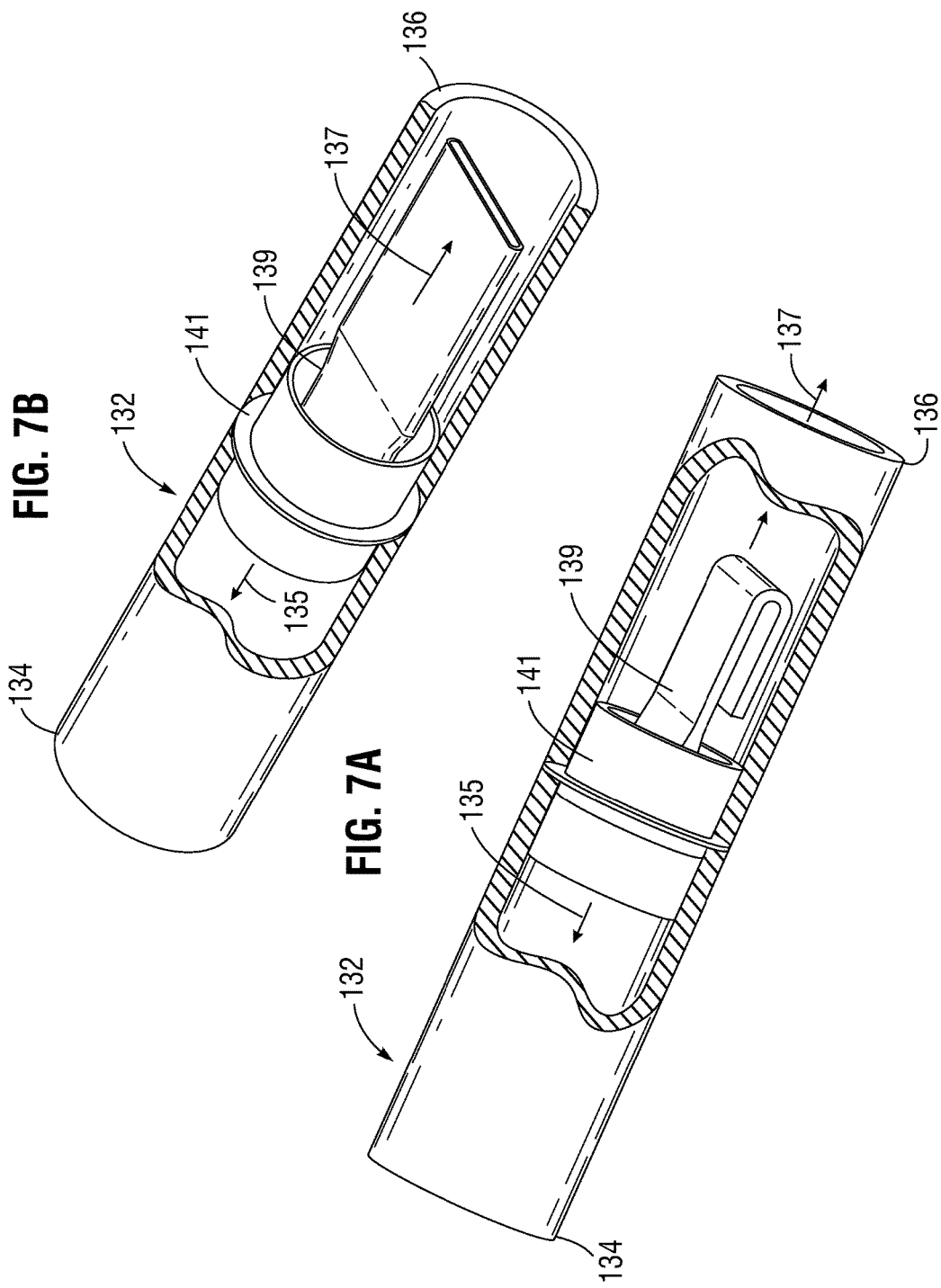

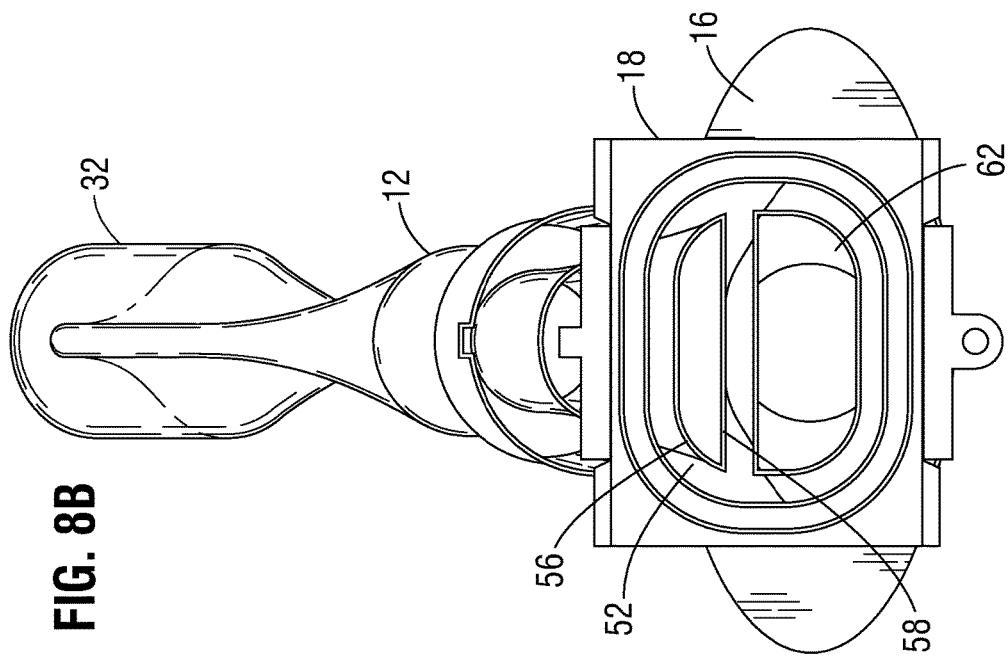
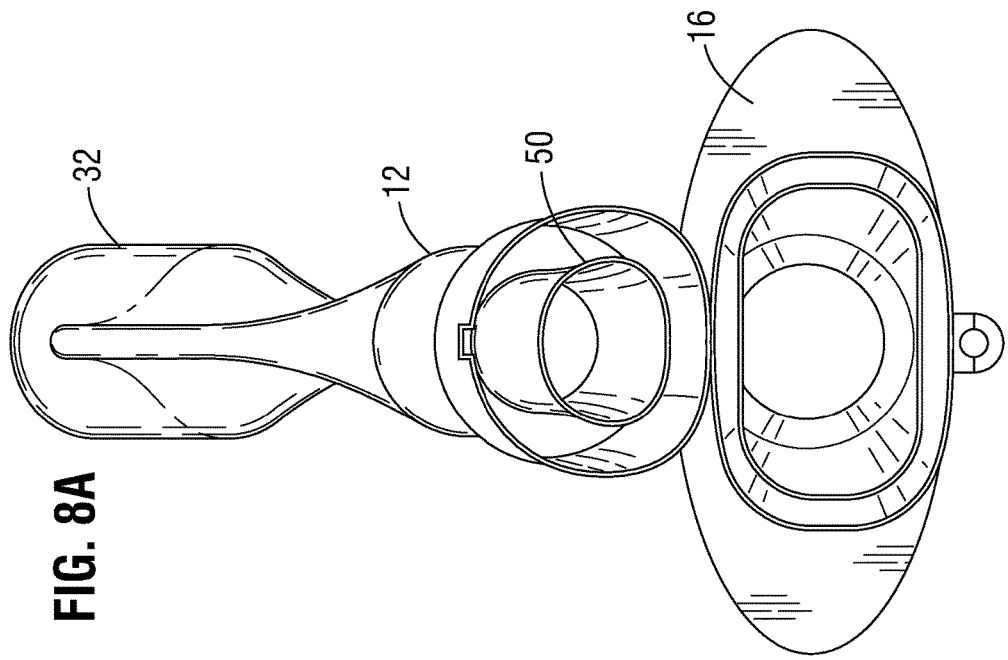

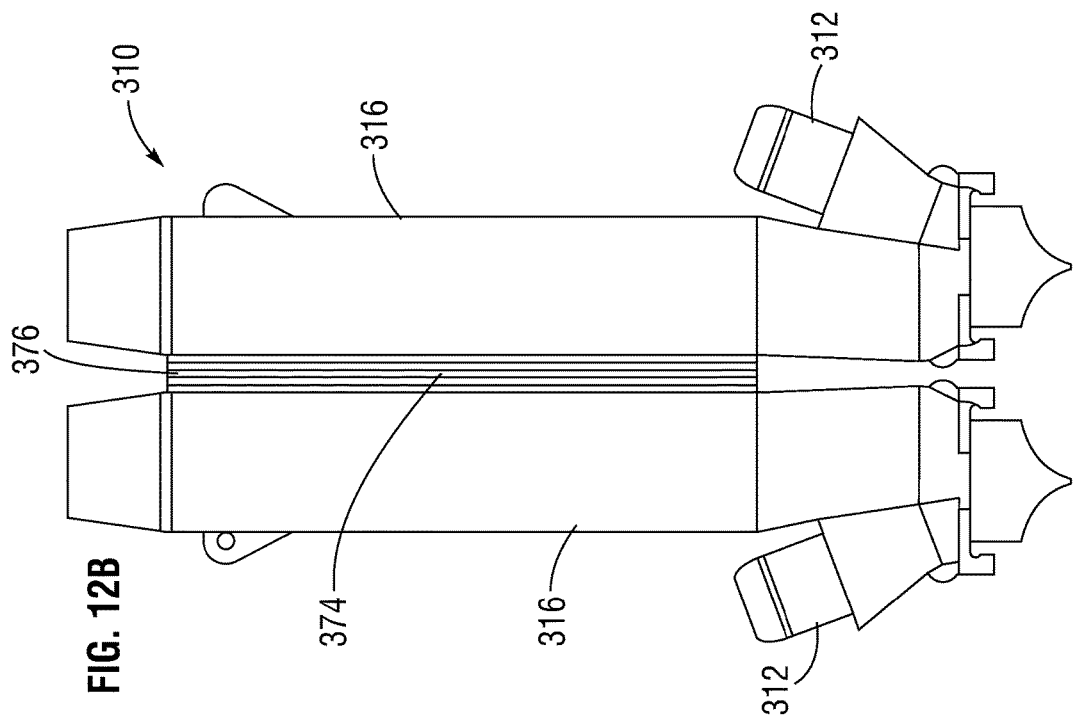
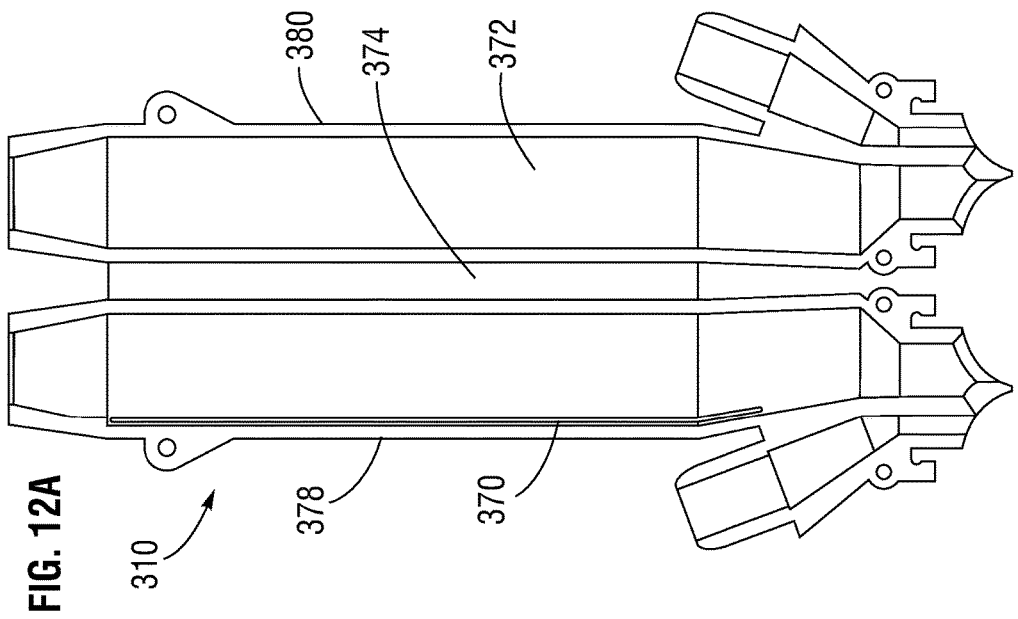
FIG. 12B
FIG. 12A

NASAL DRY POWDER DELIVERY SYSTEM FOR VACCINES AND OTHER TREATMENT AGENTS

CROSS REFERENCE TO RELATED APPLICATIONS

This is the U.S. National Stage of International Application No. PCT/US2013/047399, filed Jun. 24, 2013, which was published in English under PCT Article 21(2), which in turn claims the benefit of the earlier filing date of U.S. Provisional Application No. 61/665,778, filed on Jun. 28, 2012, which. The provisional application is incorporated herein by reference in its entirety.

STATEMENT OF GOVERNMENT SUPPORT

This invention was made by an agency of the United States Government or under a contract with an agency of the United States Government. The name of the U.S. Government agency is: the Department of Health and Human Services.

FIELD

The present disclosure is directed to methods and apparatuses for intranasal delivery of a substance to a subject.

BACKGROUND

Various devices have been developed to provide for the nasal delivery of treatment agents, such as medications or vaccines, to a subject. Aerosol delivery of drugs, vaccines, and other therapeutic, preventative, and diagnostic medical products avoids many of the drawbacks of injection, including need for skilled personnel, risk of blood-borne disease, high cost, patient aversion to injection, and the need to safely dispose of used needles and syringes. However, conventional aerosol delivery devices have significant shortcomings that prevent their widespread use. Such shortcomings include, for example, complicated device construction and operation, high cost of manufacture and use, and external power requirements.

Dry powder inhalers can be an attractive means to administer medications or vaccines since they do not require reconstitution. However, conventional dry powder inhalers have numerous shortcomings that restrict their widespread use and adoption. Accordingly, improvements in dry powder delivery devices are desirable.

SUMMARY

Various embodiments of nasal delivery devices and methods of delivering a powder to a nostril of a subject are disclosed herein. In one embodiment, a nasal delivery device includes an air-receiving section that has a first passageway therethrough to allow air to pass through the air-receiving section, a powder-reservoir receiving section sized to receive a powder reservoir, and a powder-delivery section that has a second passageway therethrough to allow aerosolized powder from the powder reservoir to pass through the powder-delivery section. The first passageway can have a first end and a second end, with the first end being further from the powder-reservoir receiving section and the second end being at or near the powder-reservoir receiving area. The second end of the air-receiving section can include a flattened region so that air exiting the air-receiving section has a generally flattened profile.

In some embodiments, the first end of the air-receiving section has a larger cross-sectional area than the second end. The first end of the air-receiving section can have a generally circular cross-sectional area. The flattened region can be at least partly defined by a curved sidewall and the curved sidewall can be configured to generally match a respective sidewall on a powder reservoir.

In some embodiments, the powder-reservoir receiving section can include at least one piercing member that is configured to engage and pierce a frangible cover of a powder reservoir. The piercing member(s) can be sized to extend into the powder reservoir and generally push the frangible cover towards at least one side wall of the powder reservoir. The piecing member(s) can be formed of two piercing members located on opposing sides of the powder-reservoir receiving section. In some embodiments, the powder-reservoir receiving section includes at least one attachment member for coupling a powder reservoir to the powder-reservoir receiving section. The attachment member(s) can include grooves that are sized to engage with a respective lip on the powder reservoir. In some embodiments this coupling is irreversible, providing an auto-disabling feature that prevents reuse of the device.

In some embodiments, an inlet tube can be coupled to the air-receiving section, with the inlet tube having a first end sized to be placed in a mouth of a user to receive air from an exhalation of the user. The inlet tube can include a visual indicator of air passing therethrough. The visual indicator can include an expandable region of the inlet tube, with the expandable region being expandable from a first, flattened configuration to a second, expanded configuration when air passes through the inlet tube. The visual indicator can also include an elongate member fastened to the inlet tube, with the elongate member being configured to change shape when air passes therethrough. The elongate member can be configured to unroll when air passes therethrough.

In some embodiments, the second passageway can have an inlet end and an exit end, with the inlet end being at or adjacent the powder-reservoir receiving section and the exit end being sized to be received in a nasal opening of a user. The inlet end of the second passageway can have a larger cross-sectional area than the flattened region of the second end of the first passageway. In some embodiments, the second passageway can include a recirculation zone, with the recirculation zone having a larger cross-sectional area than the inlet end of the second passageway.

In some embodiments, a hinge member can be provided that extends along at least a portion of the air-receiving section, the powder-reservoir receiving section, and the powder-delivery section, with the hinge member being located to allow the device to move between an open configuration for manufacture and a closed configuration for use.

In some embodiments, a powder reservoir can be configured to be coupled to the powder-reservoir receiving section. The powder reservoir can include one or more alignment markings to facilitate alignment of the powder reservoir when coupling it one or more piercing members on the powder-reservoir receiving section. The powder reservoir can include a treatment agent and, in some cases, an excipient. The excipient can be selected so that a greater portion of excipient lofts before the treatment agent.

In another embodiment, a method of delivering an aerosolized treatment agent to a subject is provided. The method can include attaching a powder reservoir containing a treatment agent to a nasal delivery device, positioning an air inlet end of the device into an air delivery source, positioning an exit end the device at least partially within a nostril of the subject, delivering air through a passageway in the air inlet end to the powder reservoir, the passageway comprising a flattened region so that air exiting the flattened region enters the powder reservoir with a generally flattened profile, and delivering aerosolized treatment agent through the exit end of the device and into the nostril of the subject.

In some embodiments, the air delivery source comprises exhaled air and the air inlet end of the device is positioned in the subject's mouth. In other embodiments, the air delivery source can comprise an external source, such as a squeeze bulb or other types of air sources (manual or powered).

In some embodiments, the act of attaching the powder reservoir to the device can include attaching a lip of the powder reservoir to one or more grooves on the device. The act of attaching the powder reservoir to the device further can include piercing a frangible cover of the powder reservoir with at least one piercing member that extends from the device.

At least one piercing member can extend into the powder reservoir and push the frangible cover towards at least one side wall of the powder reservoir.

In some embodiments, the method can include providing a visual indication when air is delivered through a passageway in the air inlet end to the powder reservoir. The act of providing a visual indication can include expanding a region of the air inlet end from a first, flattened configuration to a second, expanded configuration when air passes through the air inlet end. The act of providing a visual indication can include changing a shape of an elongate member fastened to the air inlet end when air passes therethrough. In some embodiments, the elongate member unrolls to change shape.

In some embodiments, before attaching the powder reservoir, the method comprises folding the device about a hinge member and attaching opposing surfaces on the device to one another. The attachment of opposing surfaces can include ultrasonic welding of opposing surfaces. The attachment of opposing surfaces can also include snap fitting opposing surfaces together. The attachment of opposing surfaces can also include bonding opposing surfaces together by an adhesive.

In another embodiment, a device can include a reservoir containing a treatment agent and an excipient, with the reservoir comprising a pair of opposing sidewalls that are generally curved toward one another to facilitate air flow across an inside surface of each sidewall, a sealing member for sealing the treatment agent and the excipient inside the reservoir, and an attachment member extending from the reservoir to facilitate coupling of the reservoir to a powder-reservoir receiving section of a nasal delivery device.

In some embodiments, the sealing member can include a frangible member. The frangible sealing member may be a metallic foil, polymer film, combination foil/film material, or other similar type of material. The sealing member can include one or more alignment markings to facilitate alignment of the powder reservoir when coupling the powder-reservoir receiving section. In some embodiments, the excipient can be selected so that a greater portion of excipient lofts before the treatment agent when exposed to an air flow. The excipient can also be positioned in the reservoir relative to the treatment agent so that a greater portion of excipient lofts before the treatment agent when exposed to an air flow.

The foregoing and other objects, features, and advantages of the invention will become more apparent from the following detailed description, which proceeds with reference to the accompanying figures.

BRIEF DESCRIPTION OF THE DRAWINGS

FIG. 1A is a partial side view of a nasal delivery device with a remote activation member.

FIG. 1B is a perspective view of a powder reservoir.

FIG. 4 illustrates an embodiment of a nasal powder delivery device coupled to a powder reservoir.

FIG. 6 illustrates another view of the device shown in FIG. 4.

FIGS. 7A and 7B illustrate different stages of operation of an inlet tube with a visual indicator of airflow.

FIGS. 8A and 8B illustrate cross-sectional views of a delivery device and powder reservoir, illustrating a flattening of an air receiving portion of the device.

FIGS. 12A and 12B illustrate an exemplary folding mechanism for a dry powder delivery device.

DETAILED DESCRIPTION

Figure 2B:
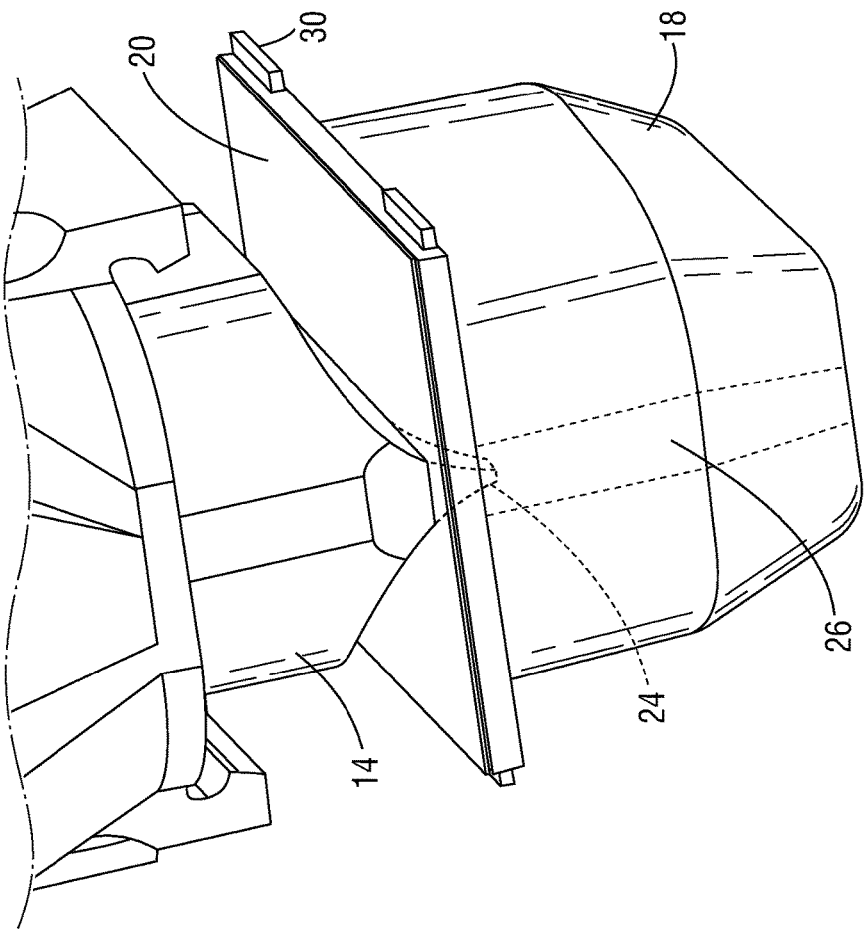
FIGS. 2A-2C illustrate partial views of a nasal delivery device being coupled to a powder reservoir.
Figure 2A:
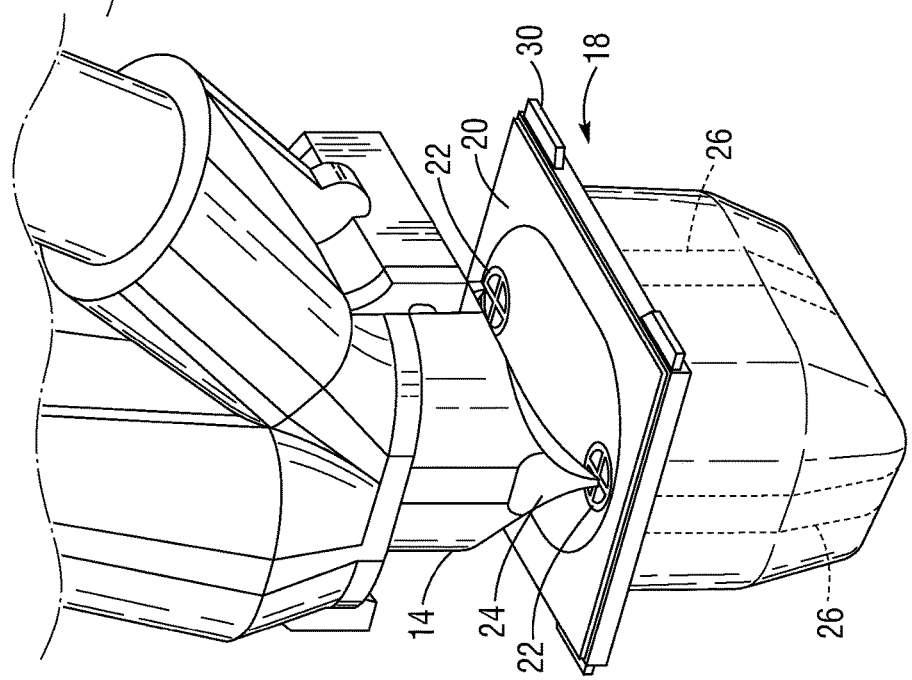
Figure 3:
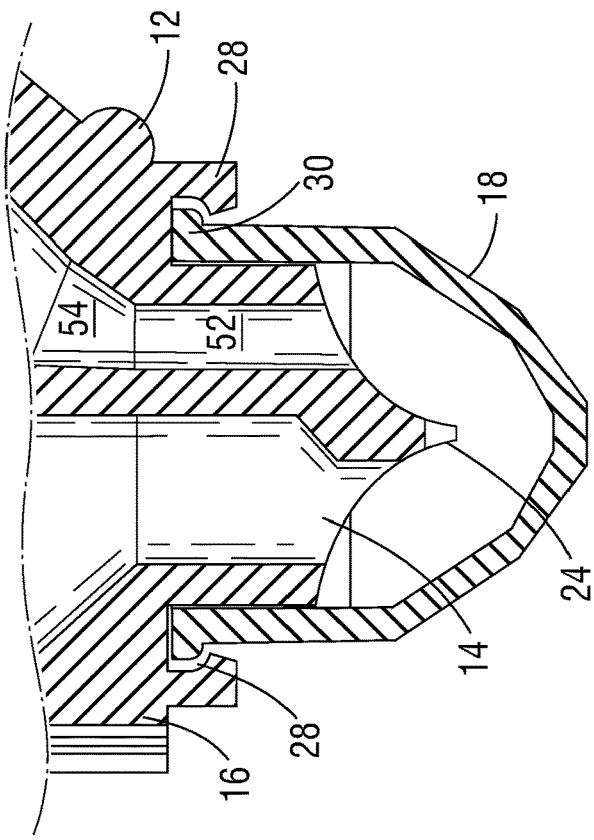
FIG. 3 illustrates a partial cross-sectional view of the nasal delivery device coupled to a powder reservoir.
Figure 2C:
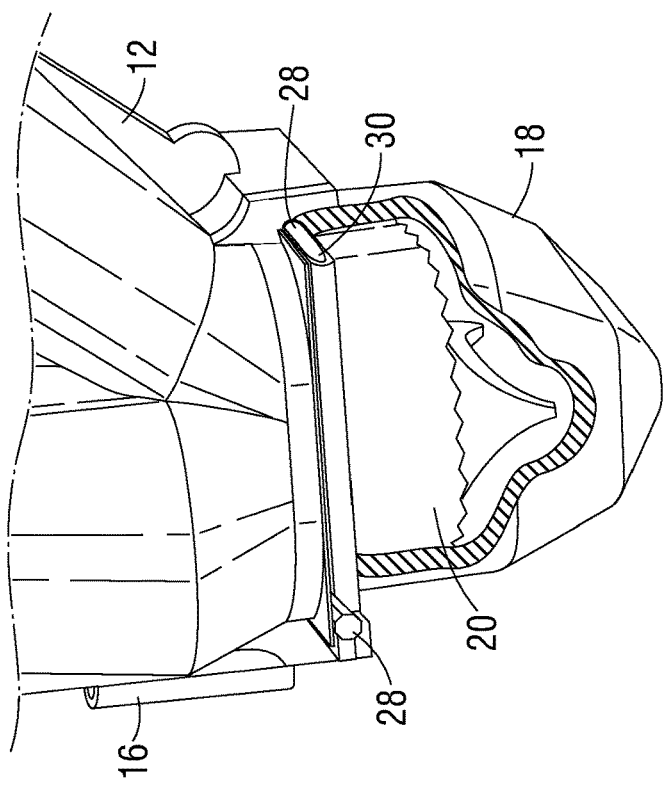

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "frangible" means capable of being broken and/or removed to allow access to materials behind or under the "frangible" member. Accordingly, a "frangible" cover on a container can be, for example, punctured or cut to obtain access to materials within the container or, alternatively, entirely or partly removed to obtain access to the materials.

Treatment agents, as used herein, comprise agents that can be administered to living organisms for an effect in the treated organism. Such agents include live and killed organisms for vaccination, immunogens, immune activators or suppressors, chemotherapeutics, pharmaceuticals, nucleic acids, insulin, hormones, antibodies and fragments thereof, receptors, proteins, carbohydrates, fats, nutrients, anesthetics, narcotics, and pain relievers.

Exemplary methods of the present disclosure comprise delivery of treatment agents such as vaccine compositions. The present disclosure contemplates the use of any vaccine composition or other treatment agents that can be delivered via the disclosed devices and/or disclosed methods of administration. Particularly preferred vaccination compositions are those for measles, mumps and rubella. Such compositions may comprise measles vaccine, mumps vaccine, rubella vaccine and combinations and mixtures such as measles and mumps, rubella and mumps, measles and rubella, and measles, mumps and rubella. Other particularly preferred vaccine compositions are those for influenza. Such compositions may comprise live virus vaccines, inactivated virus vaccines, and virus-like particle vaccines. The vaccines further comprise pharmaceutical or formulation components such as those known in the art, including, but not limited to, diluents, compounding agents, surfactants, and agents to maintain sterility.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernible, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

The embodiments described herein relate to dry powder inhalers for nasal administration of drugs, vaccines, and other therapeutic, preventative, and diagnostic medical products. In some embodiments, the powder is placed in an inhaler device from which it is lofted into the airstream of the patient by the patient's own expiratory flow for conveyance into the naris. Such nasal dry powder inhalers provide numerous advantages over conventional aerosol delivery systems, such as a nebulizer-liquid vaccine system, including, for example, their simpler construction and operation, low cost, and no need for external power. In addition, dry powder vaccines and medications can have some advantages as the delivery agent over other delivery media, such as less stringent cold chain requirements.

FIG. 1A illustrates a dry powder delivery device 10 comprising an air receiving section 12, a powder reservoir receiving section 14, and a powder delivery section 16. FIG. 1B is an exemplary powder reservoir 18, which can be secured to device 10 at powder reservoir receiving section 14.

Powder reservoir 18 can have a sealing member 20 that must be pierced or opened before powder within powder reservoir 18 can be delivered to a location outside of powder reservoir 18. Although FIG. 1B illustrates a sealing member that extends across and covers a top portion of powder reservoir 18, it should be understood that other types of sealing members can be used to seal the reservoir before use. Sealing members can be formed of various materials that are capable of substantially sealing powder within powder reservoir 18 without reacting with the powder. In the example shown in FIG. 1B, sealing member 20 comprises a foil lid.

FIGS. 2A-2C illustrate a method of coupling powder reservoir 18 to device 10. As shown in FIG. 2A, one or more alignment marks 22 can be provided on powder reservoir 18 to create a visual cue for aligning powder reservoir 18 with powder reservoir receiving section 14 to facilitate coupling of the powder reservoir 18 to device 10. In the event that powder reservoir 18 is designed to be received by powder reservoir receiving section 14 concurrently with the removal and/or piercing of sealing member 20, the alignment marks can be positioned on sealing member 20 itself. For example, as shown in FIG. 2A, two alignment marks 22 are provided on an outward facing surface of sealing member 20. Powder reservoir receiving section 14 can have two corresponding seal-cutting and/or seal-removing members (e.g., piercing members 24) that extend from the powder reservoir receiving section 14.

As shown in FIG. 2B, after aligning piercing members 24 with respective alignment marks 22, sealing member 20 can be pierced by piercing member 24 as the power reservoir 18 moves into contact with device 10 (or vice versa). If desired, respective guide members can be provided on one or both of device 10 and powder reservoir 18. For example, as shown in FIG. 1B and 2A, powder reservoir 18 can be formed with one or more grooves 26 that are configured to receive piercing members 24 and guide them along an interior surface of powder reservoir 18. In some embodiments, grooves 26 can comprise a pair of grooves that extend along opposing (facing) surfaces on the inside of powder reservoir 18.

As piercing members 24 extend into powder reservoir 18, sealing member 20 is pushed back against the walls of the inside of powder reservoir 18 as shown in FIG. 2C. An attachment mechanism can be provided to securely couple powder 18 to device 10. As shown in FIG. 2C, the attachment mechanism can comprise one or more grooves 28 along the base of powder reservoir receiving section 14 that are sized to receive a lip 30 (or rim) that extends along at least a portion of an upper surface of powder reservoir 18. Thus, when fully inserted, lip 30 snaps into grooves 28 to securely couple powder reservoir 18 to device 10. In some embodiments this coupling is irreversible, providing an auto-disabling feature to prevent reuse of the device.

FIG. 3 shows a cross-sectional view of powder reservoir 18 coupled to device 10. In FIG. 3, the piercing members 24 have pushed back sealing member 20 (not shown for clarity) along the inside wall of powder reservoir 18 and lip 30 is engaged with grooves 28. Accordingly, as shown in FIGS. 2A-2C and FIG. 3, the removal of sealing member 20 occurs during the act of attaching powder reservoir 18 to device 10. This advantageously reduces exposure of the contents of powder reservoir 18 by limiting the chances of contamination of the materials within the reservoir before use. In other embodiments, however, the sealing member can be removed (either manually or through some other tool) and then the device can be coupled to unsealed powder reservoir.

FIG. 4 illustrates device 10 coupled to powder reservoir 18. As shown in FIG. 4, an inlet tube 32 can be coupled to air receiving section 12. Inlet tube 32 can be configured to receive air from any source. In addition, inlet tube 32 can be formed with various shapes, such as a cylindrical tube, so long as inlet tube 32 has a passageway that is configured to allow air from the source to be delivered to the powder reservoir.

In one embodiment, inlet tube 32 can be configured to receive exhaled air from a user to aerosolize the powder and deliver the aerosolized powder through powder delivery section 16. Powder delivery section 16 can be tapered at a nasal insertion area 17 (e.g., a nasal prong tip) to allow comfortable insertion in a wide range of nasal orifice sizes. In addition, as shown in FIG. 4, one or more tabs 19 can be positioned at the base of the nasal insertion area 17. Tab(s) 19 can prevent over-insertion of the device into the nares, past the optimum comfortable depth. As shown in FIG. 4, nasal insertion area 17 can taper in a cylindrical manner from a larger diameter to a smaller diameter at the tip.

When configured for oral exhalation of a user, inlet tube 32 can have a first end 34 sized to receive a mouth of a user and a second end 36 configured to be coupled to air receiving section 12. Second end 36 can be coupled to air receiving section 12 in any known manner, including, for example, by a friction fit such as by sliding a slightly larger diameter of second end 36 over an outer surface of air receiving section 12 (or vice versa). One or more protrusions can be provided on surfaces of the air receiving section 12 and/or inlet tube 32 to secure the two elements together.

Figure 5:
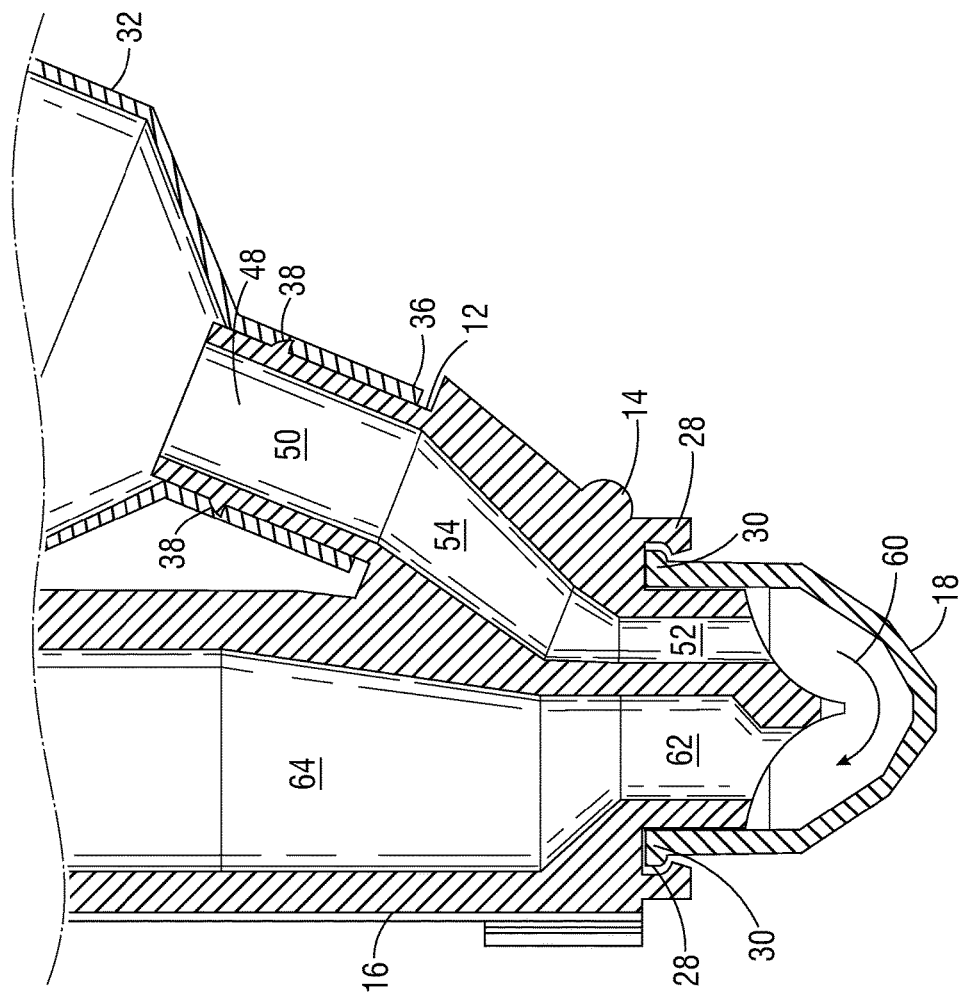
FIG. 5 illustrates a partial cross-sectional view of the device shown in FIG. 4.

FIG. 5 is a cross-sectional view of a portion of device 10 coupled to an inlet tube 32 and a powder reservoir 18. As shown in FIG. 5, inlet tube 32 has been slid over an outer surface of air receiving section 12 and protrusions 38 on air receiving section 12 are engaged with mating grooves on an outer surface of inlet tube 32 to removably secure the two elements together.

Referring again to FIG. 4, inlet tube 32 can be configured to permit exhalation, which is desirable to aerosolize the powder for delivery and restrict oral inhalation of the powder by the user. In this embodiment, various mechanisms can be provided to restrict oral inhalation of the powder. For example, FIGS. 4 and 6 illustrate inlet tube 32 with a flattened region 40 intermediate first end 34 and second end 36. As used herein, the term "flattened" or "flattened region" refers to a structure that has a first cross-sectional dimension that is significantly longer than and a second, perpendicular cross-sectional dimension. In some embodiments, the first cross-sectional dimension is at least 1/3 longer than the second cross-sectional dimension. In other embodiments, the first cross-sectional dimension is at least twice as long, and in some embodiments at least three times as long, as the second cross-sectional dimension.

Flattened region 40 can be configured so that it permits exhaled air to pass therethrough, but restricts the delivery of inhaled air in the opposite direction. For example, flattened region 40 can comprise a compliant material with a relatively thin wall that opens easily (e.g., like a balloon) when air is blown into the flattened region. However, when subjected to suction, the compliant flattened region 40 will collapse, thereby restricting inhalation by the user and delivery of powder from powder reservoir 18 into the oral cavity of the user.

Figure 14:
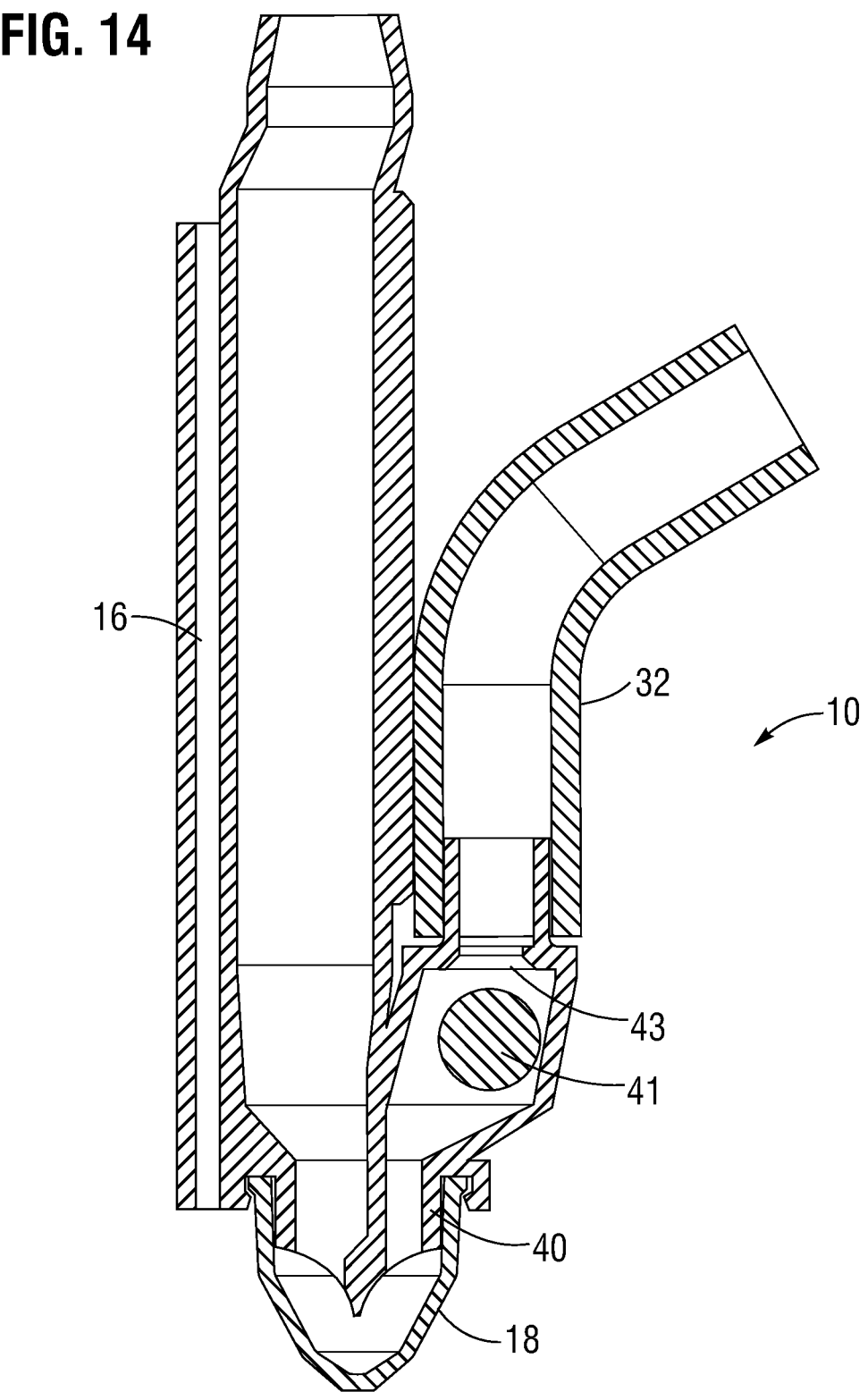
FIG. 14 illustrates another exemplary dry powder delivery device and powder reservoir.

Other types of devices to restrict oral inhalation of the powder can be provided. For example, FIG. 14 illustrates a device 10 that has a flow restricting member that is moveable on the air inlet side of device 10 between a first position that restricts air flow towards the inlet tube 32 and a second position that allows air flow towards powder reservoir 18. In the embodiment shown in FIG. 14, the flow restricting member comprises a ball 41 that is moveable into a valve seat 43 to restrict air flow towards inlet tube 32 when air is withdrawn from the inlet tube (e.g., during an inhalation). When air is directed into inlet tube through an exhalation, ball 41 moves away from valve seat 43, allowing air to pass to the flattened region 40 into powder reservoir 18.

In addition, during exhalation of the user, inlet tube 32 can provide a visual indication of the act of exhaling. For example, flattened region 40 can be configured to visually expand during user exhalation, thereby providing a visual indication that the user has exhaled into inlet tube causing delivery of aerosolized powder to the user's nasal orifice. The visual expansion of flattened region 40 can comprise, for example, a significant visual expansion of the cross-sectional area of flattened region 40, such as by expanding the cross-sectional area to double the original size or greater when a exhalation is delivered by a user that is sufficient to aerosolize the powder in powder reservoir 18 and deliver it through powder delivery section 16.

As shown in FIGS. 4 and 6, inlet tube can comprise multiple sections of different configurations. For example, first end 34 can comprise a tubular member with a generally circular cross section, flattened region 40 can comprise a flattened and/or more oval construction, and second end 36 can comprise another tubular member with a generally circular cross section. As shown in FIG. 6, flattened region 40 can also have a wider profile along the width of the flattened dimension than the tubular sections at the first and second ends 34, 36, to increase the size of the cross-sectional area of flattened region 40 during exhalation. Although first and second ends 34, 36 are shown with generally circular cross sections, it should be understood that the first and second ends 34, 36 can be provided with other shapes if desired, including, for example, oval, rectangular, etc.

FIGS. 7A and FIG. 7B illustrate another exemplary embodiment of an inlet tube 132 that is configured to restrict air flow in the inhalation direction (indicated by arrow 135) and permit air flow in the exhalation direction (indicated by arrow 137). In this embodiment, inlet tube 132 can have an elongate member 139 (e.g., a tubular streamer element) fastened or otherwise coupled to inlet tube 132 and having a passage that extends there through. In the exemplary embodiment of FIGS. 7A and 7B, elongate member 139 is fastened to an area intermediate the first end 134 and second end 136 of inlet tube 132 by an internal ring member 142. As shown in FIG. 7A, elongate member 139 is maintained in a closed, folded, and/or rolled configuration when no exhalation is applied to elongate member 139, restricting air flow through the passage of elongate member 139. If a user inhales (pulling air in the direction of arrow 135), suction on elongate member 139 is increased, further restricting the flow of air through elongate member 139. However, as shown in FIG. 7B, if an exhalation is applied to elongate member (pushing air in the direction of arrow 137), elongate member 139 can open up, unfold, and/or unroll to open the passage within elongate member 139 and permit air to pass through inlet tube 132.

In operation, elongate member 139 can also act as a visual indicator of air flow within the inlet tube. As shown in FIG. 7B, when an exhalation is applied to inlet tube 132, elongate member 139 unrolls (like a streamer) and the user or another observer (e.g., a physician or other medical staff member)

can see that the user has exhaled with sufficient force to cause air to be delivered through inlet tube 132.

In some embodiments, device 10 can be configured to direct air into the powder reservoir in a substantially flat pattern. For example, as shown in FIG. 5, device 10 comprises an air flow channel 48 that transitions from a substantially circular cross-sectional area 50 to a narrowed zone 52. Narrowed zone 52 can be, for example, an elongate slit-shaped passageway in air flow channel 48. An intermediate transition zone 54 can be provided to reduce air turbulence caused by the transition of the flow channel 48 from a circular profile (e.g., area 50) to a flattened profile (e.g., narrowed zone 52). Narrowed zone 52 can be sized to direct air through device 10 and into powder reservoir 18 in a substantially flat pattern, creating an "air knife"-type air flow profile.

FIGS. 8A and 8B are cross-sectional views taken along portions of device 10 to illustrate an exemplary transition from a non-flat cross-sectional air path (e.g., circular cross-sectional area 50) to a generally flat cross-sectional air path (e.g., slit 52). As shown in FIG. 8B, narrowed zone 52 is general defined by two side walls 56, 58. One or both side walls 56, 58 can be curved to reduce turbulence of air flow through narrowed zone 52, or to otherwise achieve a desired air flow pattern. In the embodiment illustrate in FIG. 8B, the side wall closest to the user during operation (i.e., side wall 56) is curved to generally match a shape of powder reservoir 18. For example, as shown in FIG. 1B and FIG. 5, powder reservoir 18 has side walls that curve inward at the sides as well as at the bottom of powder reservoir 18. As shown in FIG. 5, powder reservoir 18 is narrower at its bottom than at its top (e.g., where lip 30 is located). When air is directed into powder reservoir 18, the curvature of powder reservoir 18 shown in FIG. 5 can help facilitate efficient aerosolization and delivery of powder out of powder reservoir 18 as indicated by arrow 60, which indicates a general flow path of air in powder reservoir 18. As shown by arrow 60, air flowing into powder reservoir 18 undergoes a substantial reversal of direction from when it enters powder reservoir 18 to when it exits powder reservoir 18. Turbulence and fluid resistance within powder reservoir 18 can be reduced by providing a powder reservoir with one or more curved walls as illustrated herein.

Accordingly, the geometry of flow channel 48 can facilitate effective entraining of a dose of dry powder (containing medication, vaccines, etc.) into an airflow, while breaking apart agglomerations of powder into their constituent particles, without significantly increasing fluid resistance through the device.

One or more expansion zones can be provided at powder delivery section 16. For example, as shown in FIG. 5, an expansion zone 62 is provided at the outlet of powder reservoir 18 into device 10. Expansion zone 62 has a larger cross-sectional area than narrowed zone 52 to permit flow separation to allow for greater mixing of the powder within the generated airflow. In addition, expansion zone 62 can further widen into a recirculation zone 64, which can be configured to cause the largest particles to recirculate back into higher velocity flow portions of the airflow created by the user's exhalation (or other source).

Figure 9:
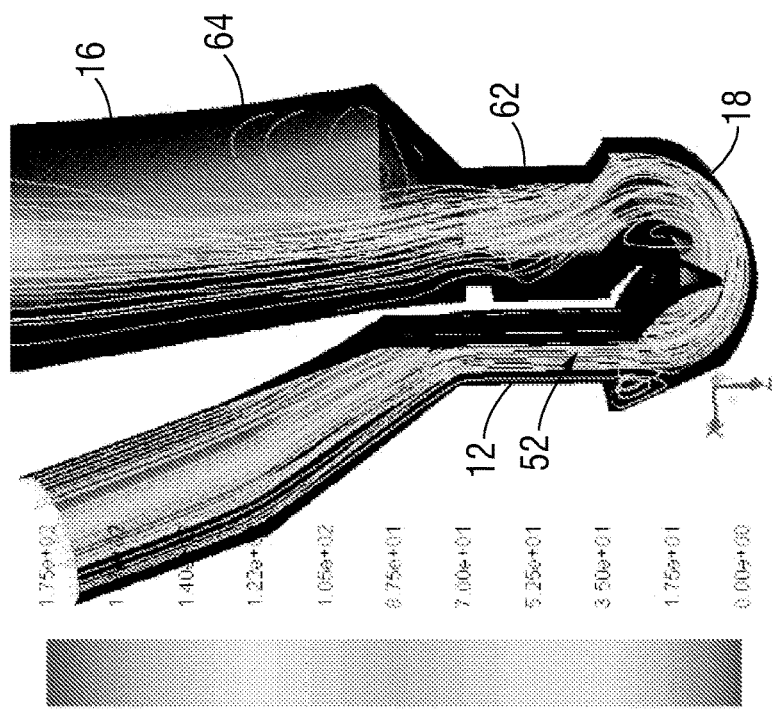
FIG. 9 illustrates a fluid flow analysis of an exemplary dry powder delivery device that utilizes a narrowed zone to deliver a flattened pattern of air flow into a powder reservoir.
Figure 10:
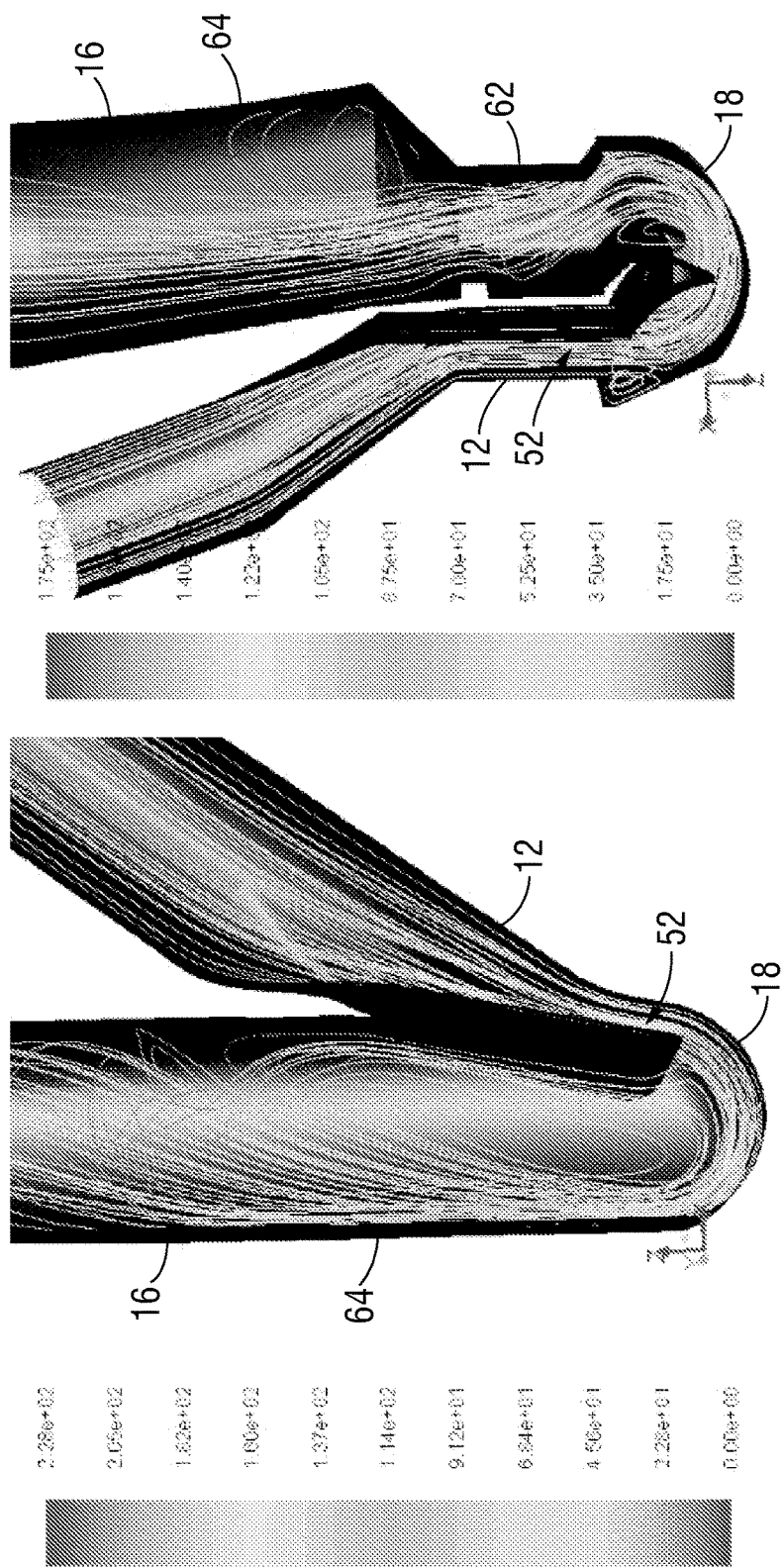
FIG. 10 illustrates another fluid flow analysis of an exemplary dry powder delivery device that utilizes a narrowed zone to deliver a flattened pattern of air flow into a powder reservoir.

FIGS. 9 and 10 illustrate fluid flow analyses for exemplary dry powder delivery devices that utilize a narrowed zone 52 to deliver a flattened pattern of air flow into powder reservoir 18. The streamlines of FIGS. 9 and 10 show a high velocity air-knife pattern of flow entering powder reservoir 18 and then expansion of the flow into recirculation zones 64. FIG. 10 illustrates a device with an expansion zone 62 before recirculation zone 64, with FIG. 9 having only a recirculation zone 64, which functions as both the expansion zone and recirculation zone. As shown in FIGS. 9 and 10, the high velocity narrowed pattern of airflow results in high lofting and effective deagglomeration of powder through powder delivery section 16.

Figure 11:
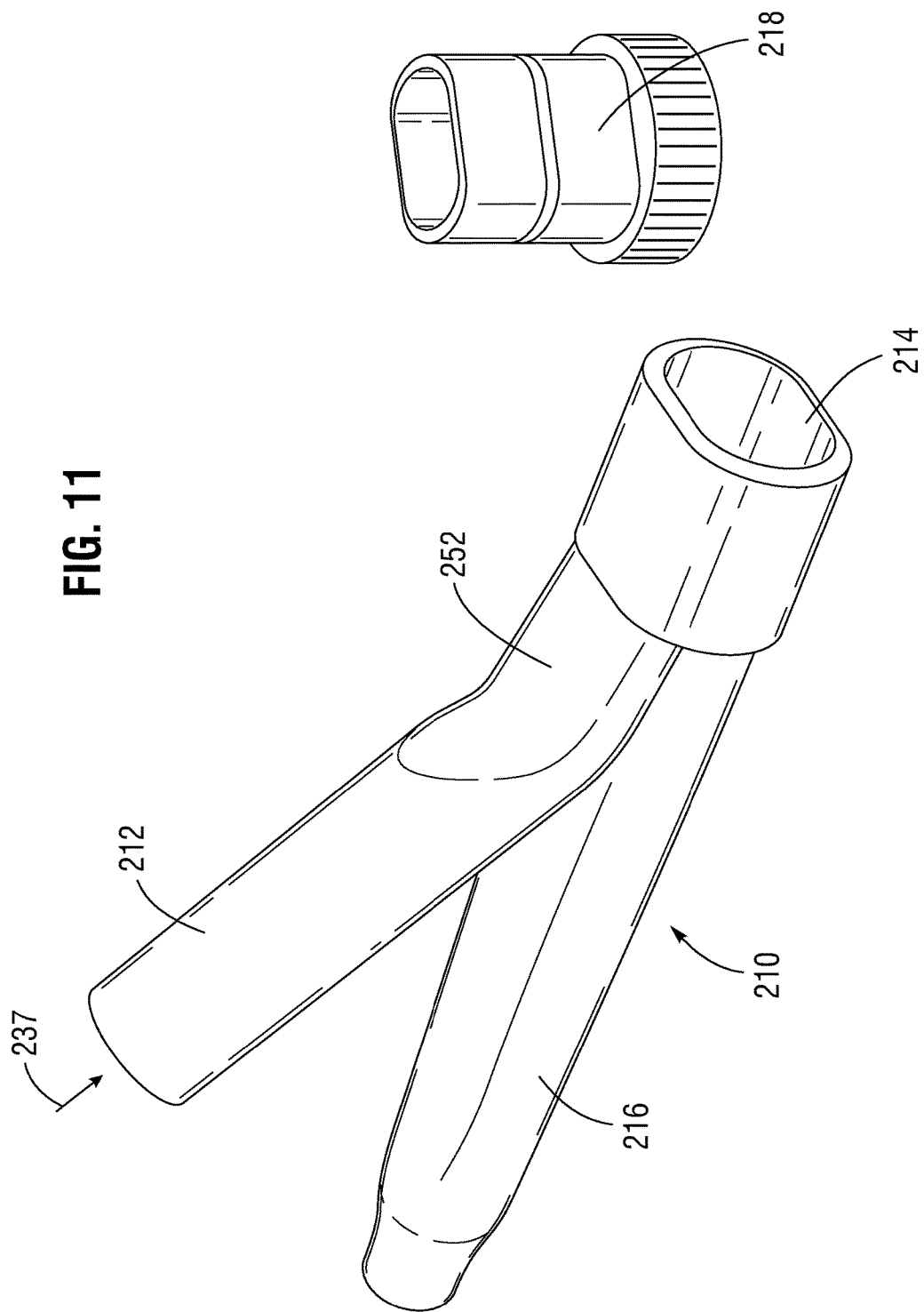
FIG. 11 illustrates another exemplary dry powder delivery device and powder reservoir.

FIG. 11 illustrates another embodiment of a device 210 that includes an air receiving section 212, a powder reservoir receiving section 214, and a powder delivery section 216. Powder reservoir 218 can be secured to device 210 at powder reservoir receiving section 214 by various known mechanical means, including, for example, a friction fit. A flattened region 252 can be provided along the air receiving section 212 to create a flattened pattern of air flow (e.g., an air-knife pattern) into powder reservoir 218 when it is coupled to device 210 and air is delivered in the direction shown by arrow 237.

Figure 13:
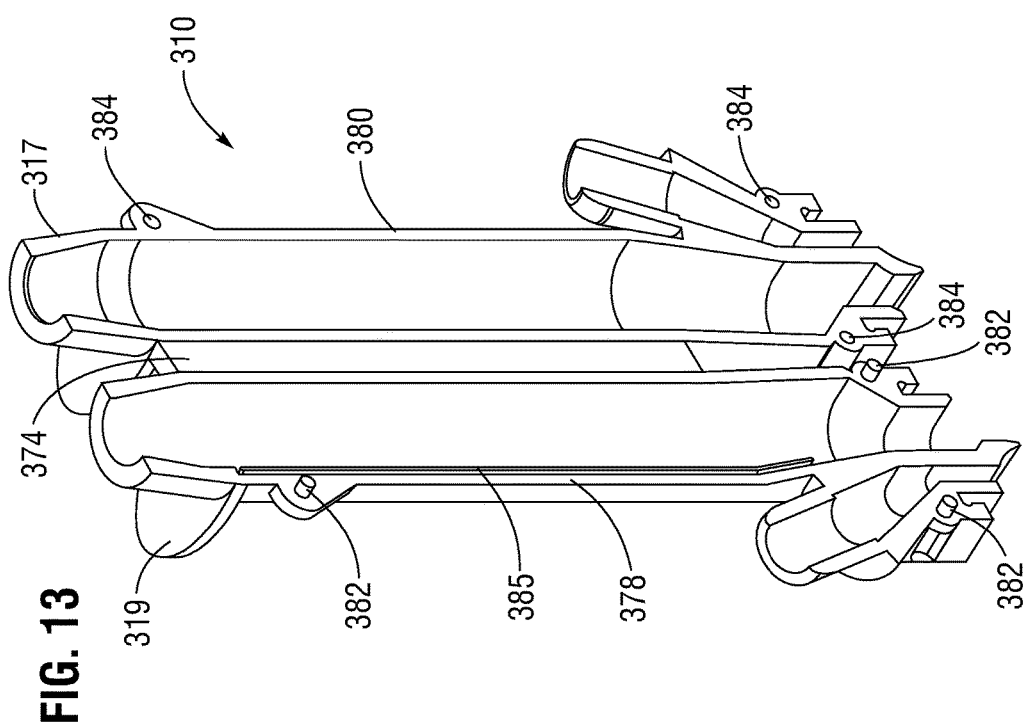
FIG. 13 illustrates an exemplary folding mechanism for a dry powder delivery device.

In some embodiments, the delivery device can be formed with a folding body as shown in FIG. 12A, FIG. 12B, and FIG. 13. FIGS. 12A and 12B illustrate front and back views of a device 310 that comprises a unitary folding body that has two sections 370, 372 coupled by a hinge member 374. Hinge member 374 can comprise a "living hinge" formed of the same material as that of sections 370, 372 to allow the device to be molded as a single piece. Hinge member 374 can be formed of a thin amount of the material of sections 370, 372 to allow hinge member 374 to bend along a line 376 of hinge member 374.

As shown in FIGS. 12A and 12B, sections 370, 372 can generally have bilateral symmetry so that after molding the unitary device 310 in a substantially flat state, sections 370, 372 can be folded about line 376 to form an operational device for receiving a powder reservoir to enable delivery of powder within the powder reservoir to a nasal orifice of a user. After folding sections 370, 372, the two sections can be secured together using various methods of attachment. For example, sections 370, 372 can be coupled together along opposing flanges 378, 380 by an adhesive or other securing method, such as ultrasonic welding. In some embodiment, energy directing features can be added at locations along the weld area (e.g., the raised ridge 385 extending generally perpendicularly from flange 378 in FIG. 13) to facilitate thermo-sonic coupling during the ultrasonic welding of the seal and to extend the seal to minimize powder loss during use.

Alternatively, or in addition, one or more physical features can be provided to secure sections 370, 372 to one another. For example, as shown in FIG. 13, one or more projections 382 can be arranged on one section in direct opposition to respective openings 384 sized to receive the projections and form a friction or "snap" fit.

By forming the device with a living hinge as described above, the device can be manufactured using a single tool and at a relatively low cost. In addition, relatively complex three-dimensional geometries, such as those shown in FIGS. 12A and 12 (and described in more detail elsewhere herein), can be formed as a unitary molded structure in a quick-cycling, multiple cavity tool.

As disclosed herein, the combination of the delivery device and the powder reservoir facilitate the deposition of medication deep into the biologically active nasal mucosae—not just on the biologically inactive epithelial tissues exterior to the nasal valve. In some embodiments, the delivery of powder in this manner can be further improved by causing an initial part of the powder dose to be delivered into the naris to coat the surfaces of the exterior nose and the nasal valve. This coating can at least partially cover the mucous layer, thereby inhibiting further capture of powder by these surfaces and enabling the bulk of the powder dose to pass through the nasal valve to desired target tissues deeper in the nasal tract.

To facilitate the delivery of powder to desired target tissues, in some embodiments, the medication can be mixed with sufficient excipient so that the excipient provides a coating function, resulting in a reduced portion of treatment agent that adheres to the nasal valve or other non-target surfaces.

The powder can be layered in the cup so excipient is preferentially lofted at the beginning of the dose to provide the coating, and the treatment agent lofts out of the cup at the end of the dose. For example, the excipient can be located in the powder reservoir at the exit area of the powder reservoir.

To further facilitate the lofting of the excipient before the medication (or other treatment agent), the excipient material can be selected so that it tends to loft before the medication. For example, if low density spray dried particles of excipient are included, these will tend to rise to the surface in the powder reservoir due to gravitational settling. Also, because of their low density and large cross-sectional area, they will loft before denser particles.

In some embodiments, an excipient material can be selected with hydrophilic porous interior, but low surface energy exteriors. Such particles will be more likely to stick to the moist nasal valve, but be less likely to capture particles of medication.

In contrast to conventional systems, the systems disclosed herein can be manufactured relatively inexpensively making them well-suited for use with single-dose disposable use as is generally preferred for vaccination. In addition, to restrict re-use of single-use disposable delivery devices, in some embodiments the powder reservoir can be configured to attach to the powder-reservoir receiving area in an irreversible fashion. For example, lips on the powder reservoir can be sized to lock with the grooves so that the powder reservoir cannot be removed from the device. This auto-disabling feature can prevent reuse of the device, which can be particularly useful in certain applications in which cross-contamination between patients is undesirable (e.g., vaccine delivery applications).

Although the devices described herein are generally intended for single-use disposable application, depending on the particular nasal delivery application, in some embodiments, the delivery devices can be cleaned and/or sterilized for reuse with a different powder reservoir 18.

In addition, conventional systems generally permit delivery of medication only to the lower respiratory tract via oral inspiration, while the disclosed systems can effectively deliver active ingredients to the nasal tract. Delivery of dry powders to the nasal cavity provides an attractive alternative to delivery to the deep lung and lower respiratory tract. Surfaces of the nasal cavity posterior to the nasal valve have significant immunologically-active tissues for the action of vaccines, and the nasal cavity provides sites where medications can be effectively transmitted to the brain.

For some dry powder medications or vaccines, delivery should be restricted to the nasal cavity, i.e., negligible powder should be inspired below the larynx into the lower respiratory tract. The dry powder devices disclosed herein can be powered by the patient's exhalation. Also, the exhalation can not only provide the air flow for delivery of the powder, it can also prevent inspiration of powder into the lower respiratory tract. Because the powder delivery is automatically timed to occur during exhalation in this situation, the exhalation flow prevents inspiration of powder into the lower respiratory tract. When combined with a means to prevent accidental oral inspiration of powder as described herein, the dry powder devices disclosed herein are well suited for use by children and others with limited ability to properly time powder delivery within the breath cycle.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A nasal delivery device comprising:
an air-receiving section that has a first passageway therethrough to allow air from an oral exhalation to pass through the air-receiving section;
a powder-reservoir receiving section sized to receive a powder reservoir; and
a powder-delivery section that has a second passageway therethrough to allow aerosolized powder from the powder reservoir to pass through the powder-delivery section, the second passageway having an inlet end and an exit end, with the inlet end being at or adjacent the powder-reservoir receiving section and the exit end being sized to be received in a nasal opening of a user, the inlet end defining an aperture out of the power reservoir,
wherein the first passageway has a first end and a second end, the first end being further from the powder-reservoir receiving section and the second end being at or near the powder-reservoir receiving section and defining an aperture into the power reservoir,
wherein the inlet end of the second passageway has a larger cross-sectional area than the flattened region of the second end of the first passageway,
wherein the second end of the air-receiving section comprises a flattened region so that air exiting the air-receiving section is directed into the powder reservoir, after the powder reservoir is received at the powder-receiving section, has a generally flattened profile, the flattened profile having a first cross-sectional dimension significantly longer than a second cross-sectional dimension, in a cross section taken along the length of the flattened region, forming an elongate slit-shaped passageway, the first cross-sectional dimension being perpendicular to the second cross-sectional dimension, and
wherein the flattened region of the air-receiving section and the inlet end of the powder-delivery section are positioned to engage with a same side of the powder reservoir.

2. The device of claim 1, wherein the first end of the air-receiving section has a larger cross-sectional area than the second end.

3. The device of claim 2, wherein the first end of the air-receiving section has a generally circular cross-sectional area.

4. The device of claim 1, wherein the flattened region is at least partly defined by a curved sidewall.

5. The device of claim 4, wherein the curved sidewall generally matches a respective sidewall on a powder reservoir that is configured to be coupled to the powder-reservoir receiving section.

6. The device of claim 1, wherein the powder-reservoir receiving section comprises at least one piercing member that is configured to engage and pierce a frangible cover of a powder reservoir.

7. The device of claim 6, wherein the at least one piercing member is sized to extend into the powder reservoir and generally push the frangible cover towards at least one side wall of the powder reservoir.

8. The device of claim 7, wherein the at least one piecing member comprises two piercing members located on opposing sides of the powder-reservoir receiving section.

9. The device of claim 1, wherein the powder-reservoir receiving section comprises at least one attachment member for coupling a powder reservoir to the powder-reservoir receiving section.

10. The device of claim 9, wherein the at least one attachment member comprises grooves that are sized to engage with a respective lip on the powder reservoir in an irreversible manner.

11. The device of claim 1, further comprising an inlet tube coupled to the air-receiving section, the inlet tube having a first end sized to be placed in a mouth of a user to receive air from an exhalation of the user.

12. The device of claim 11, wherein the inlet tube comprises a visual indicator of air passing therethrough.

13. The device of claim 12, wherein the visual indicator comprises an expandable region of the inlet tube, the expandable region being expandable from a first, flattened configuration to a second, expanded configuration when air passes through the inlet tube.

14. The device of claim 12, wherein the visual indicator comprises an elongate member fastened to the inlet tube, the elongate member being configured to change shape when air passes therethrough.

15. The device of claim 14, wherein the elongate member unrolls when air passes therethrough.

16. The device of claim 1, wherein the inlet end of the second passageway is at or adjacent the powder-reservoir receiving section and the exit end of the second passageway is sized to be received in a nasal opening of a user, the exit end being tapered to a narrower cross-sectional area at a tip portion.

17. The device of claim 1, wherein the second passageway comprises a recirculation zone, the recirculation zone having a larger cross-sectional area than the inlet end of the second passageway.

18. The device of claim 1, further comprising a hinge member that extends along at least a portion of the air-receiving section, the powder-reservoir receiving section, and the powder- delivery section, the hinge member being located to allow the device to move between an open configuration for manufacture and a closed configuration for use.

19. The device of claim 1, further comprising a powder reservoir configured to be coupled to the powder-reservoir receiving section.

20. The device of claim 19, wherein the powder reservoir has a frangible cover and the frangible cover has one or more alignment markings to facilitate alignment of the powder reservoir when coupling it to one or more piercing members on the powder-reservoir receiving section.

21. The device of claim 19, wherein the powder reservoir comprises a treatment agent.

22. The device of claim 21, wherein the powder reservoir further comprises an excipient.

23. The device of claim 22, wherein the excipient is selected and placed in the powder reservoir so that a greater portion of excipient lofts before the treatment agent.

24. The device of claim 1, further comprising a flow restricting member that is moveable between a first configuration that allows air to flow in a direction away from an air source and towards the powder reservoir and a second configuration that restricts air from flowing towards the air source.

* * * * *